United States Patent [19]

Diener et al.

[11] Patent Number: 4,613,232
[45] Date of Patent: Sep. 23, 1986

[54] MEASURING DEVICE FOR TESTING OPTICAL SYSTEMS OF AN ENDOSCOPE

[75] Inventors: Jörg Diener, Oberderdingen; Jürgen Zobel, Bretten-Sprantal, both of Fed. Rep. of Germany

[73] Assignee: Richard Wolf GmbH, Fed. Rep. of Germany

[21] Appl. No.: 584,929

[22] Filed: Feb. 29, 1984

[30] Foreign Application Priority Data

Aug. 20, 1983 [DE] Fed. Rep. of Germany ....... 3330134

[51] Int. Cl.$^4$ .............................................. G01B 9/00
[52] U.S. Cl. .................................... 356/124; 356/125
[58] Field of Search ............... 356/121, 124, 125, 127, 356/73, 73.1; 33/281, 1 BB

[56] References Cited

U.S. PATENT DOCUMENTS 1,609,895 12/1926 Troppman ........................... 356/127
2,348,858 5/1944 Sheehy ................................ 356/127
4,474,469 10/1984 Abe .................................... 356/73.1

Primary Examiner—R. A. Rosenberger
Assistant Examiner—Crystal Cooper
Attorney, Agent, or Firm—Hill, Van Santen, Steadman & Simpson

[57] ABSTRACT

A portable measuring device for testing optical systems of an endoscope consisting of a base plate, a rail with a longitudinally extending V groove for receiving a portion of the endoscope being mounted to extend parallel to the plate on a carriage movable at right angles to the groove. The device includes a vertical shaft mounted on the plate and terminating at one end in a conical point and the shaft carries at least one extension arm which is mounted to pivot in a plane parallel to the base plate. Each arm adjustably supports a measuring disk which can have its height above the plate changed or its distance from the shaft changed.

4 Claims, 3 Drawing Figures ial cone 7 and insofar as is necessary
MEASURING DEVICE FOR TESTING OPTICAL SYSTEMS OF AN ENDOSCOPE

BACKGROUND OF THE INVENTION

The present invention is directed to a measuring device for checking the geometric-optical data of an optical system for an endoscope.

In the checking of the geometric-optical data of the optical system of an endoscope for quality control during manufacturing or in the checking of the optics of an endoscope to determine if all of the specifications listed in the technical data sheet have been met, a special measuring installation, which is only found in the laboratory, is required due to the data to be measured. Thus, the known equipment makes it impractical for the inspection during a mass production of endoscopes and does not allow the inspection to be made outside of a laboratory.

SUMMARY OF THE INVENTION

The object of the present invention is to provide a device for measuring and checking geometric-optical data of an optical system for an endoscope outside of the laboratory in a simple manner.

To accomplish these objects, the present invention is directed to a device including a base plate having a planar surface, a carriage mounted on said surface of the plate for movement along a straight line and having means for holding the carriage in a fixed position on said line, a rail having a longitudinally extending V-groove for receiving a portion of the optical system of an endoscope and having means for fixing the portion therein, said rail being mounted on said carriage with the groove being parallel to the planar surface and extending perpendicular to said line, a shaft terminating at one end in a centering cone being mounted on the base plate to extend perpendicular to the planar surface with a tip of the cone lying at a lower edge of a viewing window of an endoscope received in said groove, at least one extension arm being pivotally mounted on the shaft to move in a plane extending parallel to said planar surface, said shaft having means for locking each arm in a desired angular position, a measuring disk for each arm and each arm having mounting means for exchangeably positioning the disk to extend in a plane perpendicular to the longitudinal axis of the arm and perpendicular to the planar surface, said mounting means including means to adjust the distance of the disk from the shaft and means to adjust the vertical height of the disk from the planar surface. Preferably, there are two arms with each arm having a different length and being provided with indicia to indicate the distance from the shaft. In addition, the planar surface of the plate may be provided with indicia arranged in an arc to show the angular position of each of the arms relative to the V-groove of the rail.

This device is simple in structure, portable and can be employed at any location for testing the optical systems of endoscopes. Due to the use of a measuring disk having known scales and the like, it is possible to exactly measure the angular field, the sight line, the diameter of the exit pupil, the subject field illumination, the depth of field, the focusing range, the visual lens magnification, the distortion and the resolution of the optical system of the endoscope being tested.

DESCRIPTION OF THE PREFERRED EMBODIMENTS

Figure 1:
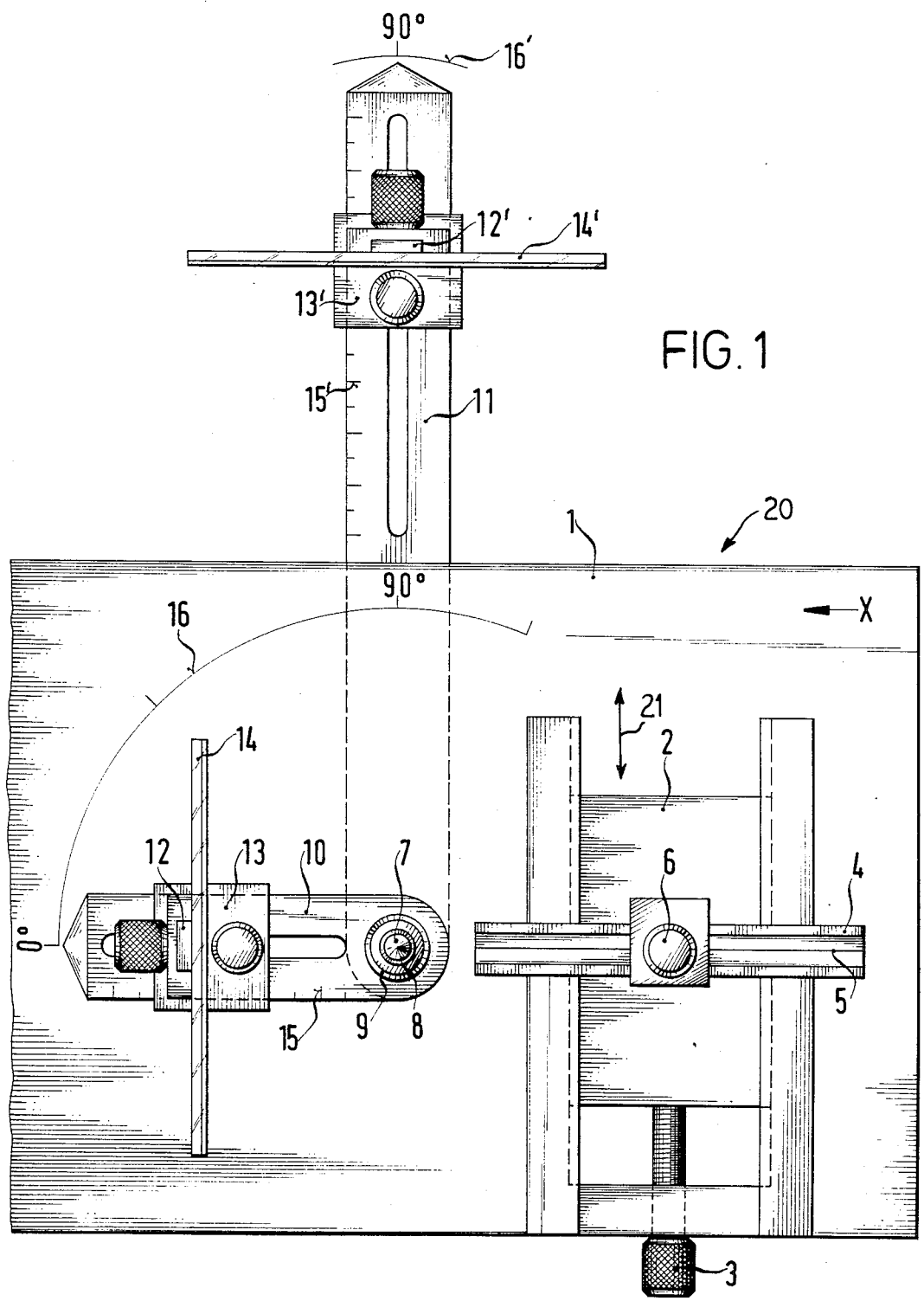
FIG. 1 is a plan view of the measuring device of the present invention.
Figure 2:
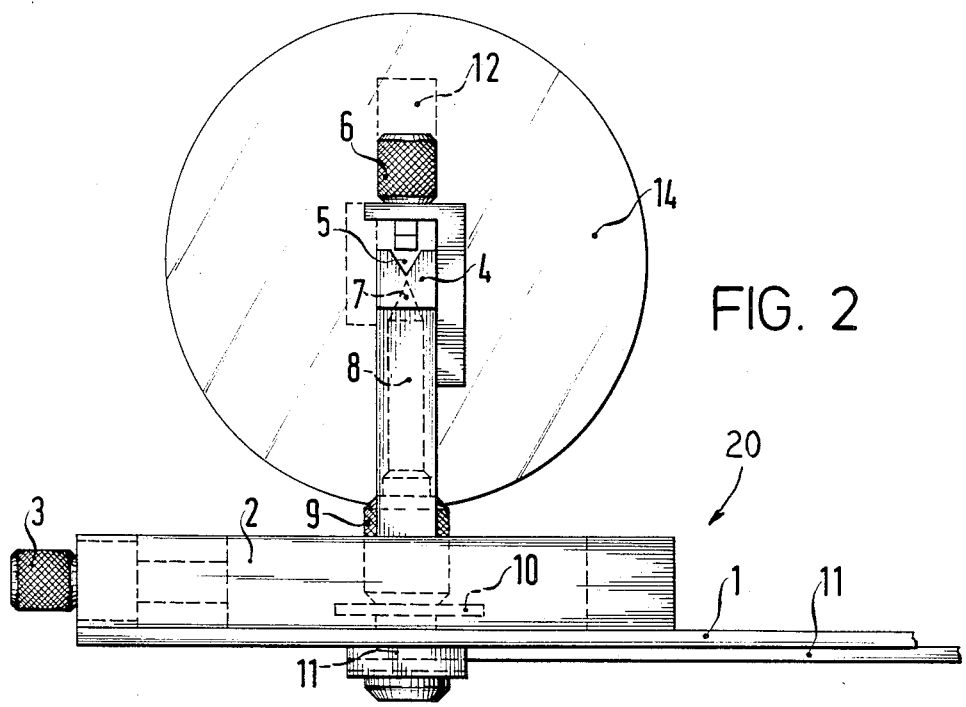
FIG. 2 is an end view taken along the direction of arrow X of FIG. 1.

The principles of the present invention are particularly useful in a device generally indicated at 20 in the drawings. The device 20 includes a base plate 1 which has a planar surface on which a carriage 2 is mounted for movement along a straight line 21. As illustrated, the carriage is displaced along the line 21 by means of a screw or threaded arrangement 3, which acts as means for holding the carriage in a fixed position on the plate 1. The carriage 2 carries a rail 4, which has on its upper surface a V-groove 5. The rail 4 is mounted on the carriage so that the V-groove 5 extends parallel to the planar surface of the base plate 1 and perpendicular or at right angles to the direction 21. The V-groove 5 is for receiving a portion of the optical system (not illustrated) of an endoscope and is preferably provided with means 6 for fastening the portion therein. The means 6 is illustrated as being a screw-type device but it can be replaced by known quick-action clamping means.

Figure 3:
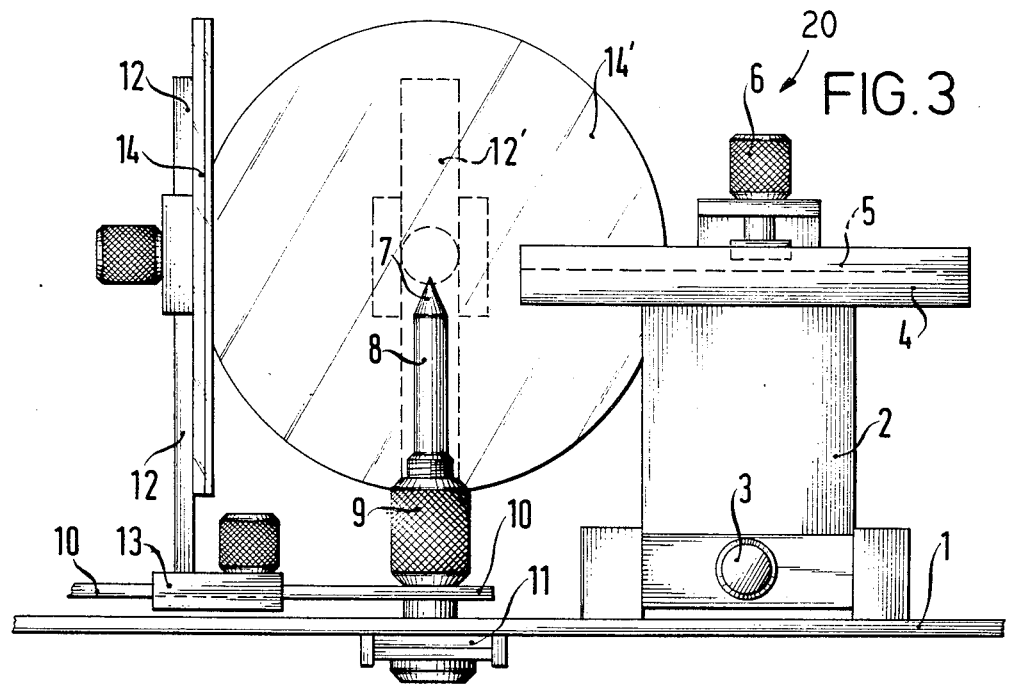
FIG. 3 is a side view taken along a direction perpendicular to the arrow X.

Adjacent to the rail 4, a shaft 8 is mounted to extend perpendicular to the planar surface of the plate 1 and terminates at one end in a centering cone 7. The shaft is either rigidly connected to the base plate or releasably connected by a means for fixing 9. Two radial extension arms 10 and 11 which have different lengths are mounted on the shaft to extend parallel to the planar surface of the base plate 1 and to pivot around the axis of the shaft 8 within two arcuate scale regions 16 and 16'. The means for fixing 9 can be used to lock each of these arms in the desired angular position. The arm 10 is provided with a measuring disk 14 and means for mounting the measuring disk on the arm. As illustrated, the means for mounting include a vertical strut or stay 12 which extends from a lockable carriage 13 that is displaceable along the arm 10 to vary the distance of the strut 12 from the shaft 8 and these distances are measured on a scale 15 on the arm 10. The mirror 14, as best illustrated in FIG. 3, is fixedly mounted on the strut 12 so that the vertical height of the mirror can be adjusted from the planar surface of the plate 1. The carriage 13 with the strut 12 and the associated screw clamps forms means to adjust the distance of the mirror from the shaft as well as means to adjust the distance or height of the mirror from the planar surface. In a similar manner, the arm 11 has a carriage 13' with a strut 12' for positioning the measuring disk 14'. The distance of the mirror 14' from the shaft can be indicated by a scale 15' on the arm 11.

In order to utilize the device 20, an endoscope with an optical system with a lateral sight line is placed in the V-shaped groove 5 and is turned in the groove until the lens viewing window is pointing in the direction of the measuring disk and extends perpendicular to the planar surface of the base plate 1. While in this position, the endoscope is displaced as far as possible in the direction toward the tip of the cone 7 and insofar as is necessary is shifted perpendicular along the line 21 by movement of the carriage 2 until the outside surface and the center of the lens viewing window come to lie on an imaginary line which would be in the extension of the axis of the shaft 8 through the point of the cone 7. Subsequently, the optical system of the endoscope can be releasably locked in the aligned position by the fixing device 3 and the clamp 6. Then the measurements are carried out.

The geometric-optical data of the optical system given an adjustable interval of the measuring disk to the axis of the shaft 8 can then be directly read from the respective measuring disk 14 and 14'. It should be noted that each of the measuring disks can be interchangeable and that the data can be computationally computed with the assistance of the measuring disk.

When the endoscope is provided with a straight view, then the respective disk 14 coming into consideration for reading the data must be set by means of pivoting the extension arm 10 or 11 until the plane of the disk extends perpendicular to the inserted endoscope. The endoscope is then placed in the V-shaped groove 5 and aligned in a manner analogous to the above explanation.

Although various minor modifications may be suggested by those versed in the art, it should be understood that we wish to embody within the scope of the patent granted hereon, all such modifications as reasonably and properly come within the scope of our contribution to the art.

We claim:

1. A device for measuring and checking geometric-optical data of an optical system of an endoscope, said device including a base plate having a planar surface, a carriage mounted on said surface of the plate for movement along a straight line and having means for holding the carriage in a fixed position on said line, a rail having a longitudinally extending V groove for receiving a portion of the optical system of an endoscope and having means for fixing the portion therein, said rail being mounted on said carriage with the V-groove being parallel to said planar surface and extending perpendicular to said line, a shaft terminating at one end in a centering cone being mounted on the base to extend perpendicular to the planar surface with a tip of the cone lying on a lower edge of a viewing window of an endoscope being received in said groove, at least one extension arm being pivotally mounted on the shaft to move in a plane extending parallel to the planar surface, said shaft having means for locking each arm in the desired angular position, measuring disks for each arm and each arm having mounting means for positioning the disk to extend in a plane perpendicular to the longitudinal axis of the arm and perpendicular to the planar surface, said mounting means including means to adjust the distance of the disk from the shaft and means to adjust the vertical height of the disk from the planar surface.

2. A device according to claim 1, which includes an additional extension arm being pivotally mounted on the shaft for rotation therealong, both of said arms being locked in angular positions by said means for locking.

3. A device according to claim 2, wherein the additional arm has a different length than the first-mentioned arm.

4. A device according to claim 1, which includes a first and second extension arm with the second extension arm having a length different than the first extension arm, each of said extension arms having a separate scale indicating the distance of the disk from said shaft, said means for locking holding each of the arms in the desired angular position.

* * * * *